United States Patent [19]

Gardner

[11] 4,322,370
[45] Mar. 30, 1982

[54] POLYCYCLIC COMPOUNDS

[75] Inventor: Derek V. Gardner, Bishop Stortford, England

[73] Assignee: Beecham Group Limited, England

[21] Appl. No.: 877,303

[22] Filed: Feb. 13, 1978

Related U.S. Application Data

[63] Continuation of Ser. No. 706,758, Jul. 19, 1976, abandoned.

[30] Foreign Application Priority Data

Jul. 24, 1975 [GB] United Kingdom ............... 30923/75

[51] Int. Cl.³ ..................... C07C 91/14; C07C 93/06
[52] U.S. Cl. ........................ 260/501.18; 260/348.19; 260/348.45; 260/348.63; 260/501.19; 424/316; 424/330; 544/106; 560/104; 562/491; 564/337; 564/338; 568/327; 568/659
[58] Field of Search ................. 260/570.7 R, 570.7, 260/501.18, 501.19; 564/337, 338

[56] References Cited

U.S. PATENT DOCUMENTS

| | | | |
|---|---|---|---|
| 2,820,817 | 1/1958 | Sam | 260/570.7 X |
| 3,388,121 | 6/1968 | Pribyl et al. | 260/570.7 X |
| 3,476,767 | 11/1969 | Bencze | 260/570.7 X |
| 3,565,956 | 2/1971 | Schulenberg et al. | 260/570.7 |
| 3,641,152 | 2/1972 | Shavel, Jr. et al. | 260/570.7 |
| 3,671,530 | 6/1972 | Van Dyke | 260/570.7 X |
| 3,988,475 | 10/1976 | Manghisi et al. | 260/570.7 X |

*Primary Examiner*—Robert V. Hines
*Attorney, Agent, or Firm*—Jacobs & Jacobs

[57] ABSTRACT

Compounds of the formula (II):

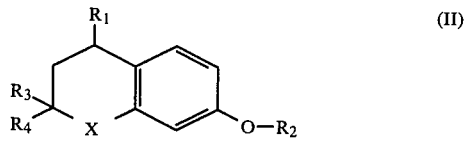

(II)

and pharmaceutically acceptable salts thereof, wherein $R_1$ is phenyl or naphthyl or substituted phenyl or naphthyl group; $R_2$ is:

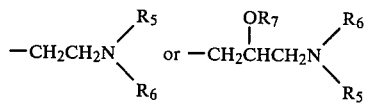

wherein $R_5$ is hydrogen or $C_{1-6}$ alkyl, $R_6$ is hydrogen or $C_{1-6}$ alkyl, phenyl, tolyl or benzyl and $R_7$ is hydrogen; $R_3$ and $R_4$ are each hydrogen atom or $C_{1-4}$ alkyl, and X is CO, CHOH, CHCl or C=C $R_8$ $R_9$ wherein $R_8$ and $R_9$ are each hydrogen or $C_{1-4}$ alkyl; or $CR_{10}OH$ or $CHR_{10}$, wherein $R_{10}$ is $C_{1-4}$ alkyl, have been found to be mood-modifying agents and anorexic agents.

24 Claims, No Drawings

POLYCYCLIC COMPOUNDS

CROSS-REFERENCE

This is a continuation of Ser. No. 706,758, filed July 19, 1976, now abandoned.

The present invention relates to novel compounds, to their preparation and to pharmaceutical compositions containing them.

Belgian Pat. No. 831939 and Belgian Patent Application No. 167446 describe inter alia compounds of the formula (I):

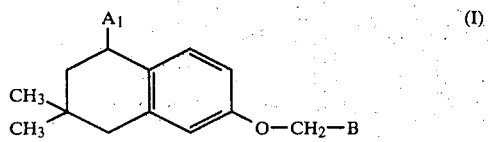

and salts thereof wherein $A_1$ is an aryl group, and B represents a group

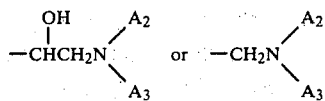

wherein $A_2$ and $A_3$ are each a hydrogen atom or $C_{1-6}$ alkyl groups. These compounds were disclosed as having useful activity as anorexic agents and mood modifying agents.

There have now been discovered another distinct group of compounds related to those of formula (I) which also have useful activity as anorexic agents and mood modifying agents and in particular have useful activity as mood modifying agents.

Accordingly the present invention provides compounds of the formula (II):

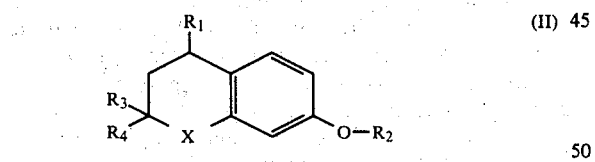

and salts thereof wherein $R_1$ is a phenyl or naphthyl group or a substituted phenyl or naphthyl group; $R_2$ is a group:

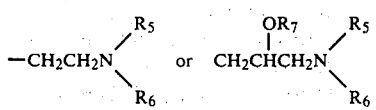

wherein $R_5$ is a hydrogen atom or a $C_{1-6}$ alkyl group, $R_6$ is a hydrogen atom or $C_{1-6}$ alkyl, phenyl, tolyl or benzyl group or $R_5$ is linked to $R_6$ so that the $NR_5R_6$ moiety is a 5-, 6- or 7-membered ring and $R_7$ is a hydrogen atom or is joined to $R_5$ to form part of a morpholine ring; $R_3$ and $R_4$ are each a hydrogen atom or a $C_{1-4}$ alkyl group, and X is CO, CHOH, CHCl or

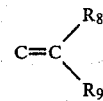

group wherein $R_8$ and $R_9$ are each a hydrogen atom or a $C_{1-4}$ alkyl group; or a $CR_{10}OH$ or $CHR_{10}$ group wherein $R_{10}$ is a $C_{1-4}$ alkyl group.

By the term substituted phenyl or naphthyl group is meant a phenyl or naphthyl group substituted by one or two halogen atoms, $C_{1-4}$ alkyl, $C_{1-4}$ alkoxy, trifluoromethyl, nitro, cyano, hydroxy, amino, dimethylamino, diethylamino, carboxamido, trifluoromethylthio or sulphonamido groups.

Suitably $R_1$ is a phenyl group substituted by a fluorine, chlorine or bromine atom or a nitro or trifluoromethyl group, or a naphthyl group.

Most suitably $R_1$ is a phenyl group substituted by a fluorine or chlorine atom or a trifluoromethyl group, or a naphthyl group.

Suitably $R_3$ and $R_4$ are each hydrogen or methyl groups and preferably $R_3,R_4$ are each methyl groups.

Suitably $R_5$ is a hydrogen atom or a methyl group and preferably $R_5$ is a methyl group.

Suitably $R_6$ is a hydrogen atom or a methyl, ethyl or benzyl group and preferably $R_6$ is a methyl group.

Suitably $R_7$ is a hydrogen group.

Suitably $R_8$ is a hydrogen atom or a methyl group.

Suitably $R_9$ is a hydrogen atom or a methyl group.

Preferably $R_8$ and $R_9$ are both hydrogen atoms.

Particularly suitable values of $R_2$ include those of the sub-formulae (a)-(e):

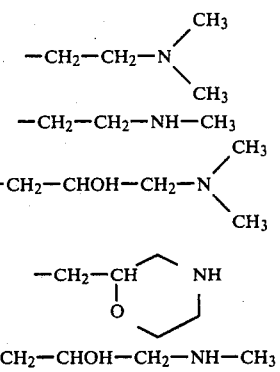

Suitably X is a CO,

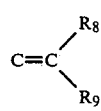

or a $CHR_{10}$ group wherein $R_8$ and $R_9$ are each a hydrogen atom or a $C_{1-4}$ alkyl group and $R_{10}$ is a $C_{1-4}$ alkyl group.

A preferred group of compounds of the formula (II) are those of the formula (III):

(III)

and salts thereof wherein X, $R_2$, $R_3$, and $R_4$ are as defined in relation to formula (II); $R_{11}$ is a chlorine, bromine or fluorine atom or a trifluoromethyl, nitro, cyano, carboxamido or sulphonamido group; $R_{12}$ is a hydrogen atom or $R_{11}$ and $R_{12}$ are both chlorine or fluorine atoms.

Preferably $R_2$ is a group of the sub-formulae (f)–(i):

$$-CH_2-CH_2-N(CH_3)_2 \quad (f)$$

$$-CH_2-CH_2-NHCH_3 \quad (g)$$

$$-CH_2-CHOH-CH_2-N(CH_3)_2 \quad (h)$$

$$-CH_2-CHOH-CH_2-NHCH_3 \quad (i)$$

Preferably $R_3$ and $R_4$ are each methyl groups.

Most suitably $R_{11}$ is a chlorine or fluorine atom or a trifluoromethyl group.

Preferably $R_{11}$ is a chlorine or fluorine atom.

Preferably $R_{12}$ is a hydrogen atom.

Certain particularly suitable sub-groups of compounds of the formula (II) include those of formulae (IV)–(VIIb):

(IV)

(V)

(VI)

(VII)

(VIIa)

(VIIb)

and salts thereof wherein $R_{13}$ is a fluorine or chlorine atom or a nitro or trifluoromethyl group and $R_{14}$ is a hydrogen atom or a methyl, ethyl or benzyl group.

Suitably $R_{13}$ is a fluorine or chlorine atom.

Suitably $R_{13}$ is a trifluoromethyl group.

More suitably $R_{13}$ is a 4-chlorine atom.

More suitably $R_{13}$ is a 4-fluorine atom.

More suitably $R_{13}$ is a 3-trifluoromethyl group.

Preferably $R_{13}$ is a 4-chlorine or 4-fluorine atom.

Preferably $R_{14}$ is a methyl group.

Since the compounds of this invention are nitrogenous bases they are able to form acid addition salts in conventional manner. Normally, such salts are those formed from pharmaceutically acceptable organic or inorganic acids such as citric, acetic, propionic, lactic, tartaric, mandelic, succinic, oleic, glutaric, gluconic, methanesulphonic, toluenesulphonic, sulphuric, phosphoric, hydrobromic or hydrochloric acid. Preferred compounds of this invention include:

4-(4-chlorophenyl)-2,2-dimethyl-7-(2-dimethylaminoethoxy)-1-tetralone 4-(4-chlorophenyl)-1-hydroxy-2,2-dimethyl-7-(2-dimethylaminoethoxy)tetralin 1-chloro-4-(4-chlorophenyl)-2,2-dimethyl-7-(2-dimethylaminoethoxy)tetralin 4-(4-chlorophenyl)-2,2-dimethyl-7-(2-dimethylaminoethoxy)-1-methylidene tetralin 4-(4-chlorophenyl)-1,2,2-trimethyl-7-(2-dimethylaminoethoxy)tetralin 4-(3-trifluoromethylphenyl)-2,2-dimethyl-7-(2-dimethylaminoethoxy)-1-tetralone 4-(4-fluorophenyl)-2,2-dimethyl-7-(2-dimethylaminoethoxy)-1-tetralone 4-(4-chlorophenyl)-7-(2-hydroxy-3-dimethylaminopropoxy)-2,2-dimethyl-1-tetralone 4-(4-chlorophenyl)-7-(2-hydroxy-3-methylamino-propoxy)-2,2-dimethyl-1-tetralone
4-(4-chlorophenyl)-7-(2-benzylmethylaminoethoxy)-2,2-dimethyl-1-tetralone
4-(4-chlorophenyl)-2,2-dimethyl-7-(2-methylaminoethoxy)-1-tetralone
4-(3,4-dichlorophenyl)-2,2-dimethyl-7-(2-dimethylaminoethoxy)-1-tetralone
4-(3,4-dichlorophenyl)-7-(2-hydroxy-3-methylaminopropoxy)-2,2-dimethyl-1-tetralone, and their salts.

Compounds within the formula (II) affect the central nervous system. Thus depending on the dosage used, certain compounds of the formula (II) are able to produce anorexic or mood modifying effects in mammals. In particular compounds within the formula (II) are useful as anti-depressants for humans and at a higher dose are useful as anorexic agents.

Accordingly, in one of its aspects the present invention provides pharmaceutical compositions which comprise a compound of this invention together with a pharmaceutically acceptable carrier.

Normally, the compositions of this invention are adapted for oral administration to humans although compositions adapted for parenteral administration are also envisaged.

The most suitable dosage forms are unit dosage forms such as tablets, capsules, sachets and the like which contain a predetermined quantity of active material.

Such unit dosage forms normally contain from 0.05 to 200 mg. of active material and may be taken once a day or several times a day according to the dose desired. Generally a human adult will be administered from 0.5 to 200 mgs. per day, for example, from 1 to 100 mgs.

When the composition of this invention is used for mood modification such as anti-depressant effects, it is likely that it will be used as a solid unit dosage form which contains from 0.1 mg. to 50 mg. of active ingredient, for example, 0.5 mg to 25 mg. of active ingredient.

In a further aspect this invention provides a method of reducing depression, which comprises administering an effective amount of a compound of this invention.

When the composition of this invention is used as an anorexic agent it will be used as a solid unit dosage form which contains from 0.5 mg. to 100 mg. of active ingredient, for example, 1 mg. to 50 mg. of active ingredient.

In a further aspect this invention provides a method of suppressing appetite which comprises administering an effective amount of a compound of this invention.

The present invention also provides processes for the preparation of the compounds of this invention.

The compounds of the formula (II) may be prepared from the corresponding compound of the formula (VIII):

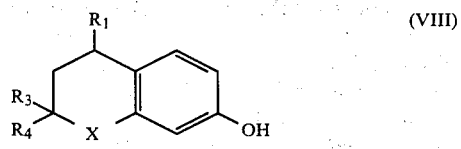
(VIII)

and salts thereof wherein X, $R_1 R_3$ and $R_4$ are as defined in relation to formula (II) by reaction with an etherifying agent such as that of the formula $QR_2$ or an acid addition salt thereof wherein $R_2$ is as defined in relation to formula (II) and Q is a readily displaceable group.

This is not a particularly suitable method of preparing compounds of the formula (II) wherein X is CHCl.

Suitable groups Q which are those which are readily displaced by nucleophilic groups and include the chlorine, bromine and iodine atoms and the hydroxyl group esterified by methane sulphonic, toluene sulphonic or like acid, activated ester groups such as the $O.CO.CH_3$, $O.CO.C_2H_5$ or like hydrocarbyloxycarbonyloxy groups.

Particularly suitable groups Q include the chlorine, bromine and iodine atoms and the methanesulphonyl and toluenesulphonyl groups.

The etherification reaction will normally be carried out in an inert solvent. Suitable solvents include hydrocarbons such as toluene or xylene, ethers such as dimethoxyethane or dimethoxypropane, ketones such as acetone, alcohols such as ethanol and other conventional solvents.

If desired the anion of the compound of formula (VII) may be produced before the etherification reaction or may be produced in situ by reaction with a base such as NaH or the like.

Generally any non-extreme temperature is used, but the reaction is substantially complete in a conveniently short time if an elevated temperature is used. For example, the reaction may be carried out at from about 0°–180° C., preferably in the region of 50°–120° C.

The compounds of formula (VIII) may be prepared by the demethylation of the corresponding compound of the formula (IX):

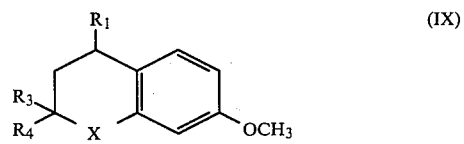
(IX)

brought about by treatment with a strong acid such as hydrobromic acid.

A further method of preparation of the compounds of the formula (II) comprises the reaction of an amine $R_5R_6NH$ with a compound of the formula (IX):

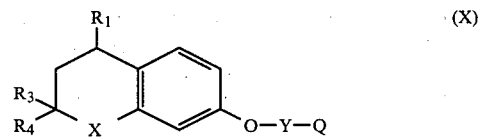
(X)

wherein $R_1R_3R_4$ and X are as defined in relation to formula (II), Y is a

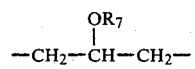

or $-CH_2-CH_2-$ group wherein $R_7$ is as defined with respect to formula (II) and Q is a readily displaceable group or when it is required to form a compound of the formula (II) wherein $R_7$ is a hydrogen atom Q may be taken together with Y to form a

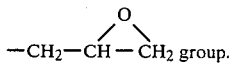 group.

Suitable displaceable groups Q include those as defined in relation to formula (VIII).

Such a reaction may take place at any non-extreme temperature, for example, 0° C.–180° C., but generally ambient or moderately elevated temperatures, for example, 12° C.–100° C. are particularly suitable.

The displacement reaction normally takes place in an organic solvent such as ethanol, ether or the like.

Compounds of the formula (II) wherein X is C=CR$_8$R$_9$ may be prepared by the reaction of a compound of the formula (XI):

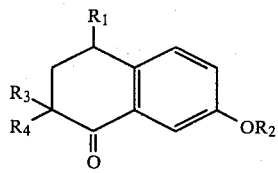

or a salt thereof wherein R$_1$R$_2$R$_3$R$_4$R$_8$R$_9$ are as defined with respect to formula (II), with a Wittig reagent.

Suitable Wittig reagents are those of the formula Ph$_3$P=CR$_8$R$_9$.

The reaction will normally be carried out in an anhydrous aprotic solvent in the absence of oxygen at a temperature between 0° C. and 100° C.

Compounds of the formula (II) wherein X is C=CR$_8$R$_9$ may also be prepared from compounds of the formula (XII):

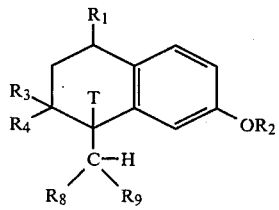

wherein R$_1$R$_2$R$_3$R$_4$R$_8$ and R$_9$ are as defined with respect to formula (II) and T is a chlorine, bromine or iodine atom or a OR$_{15}$ group wherein R$_{15}$ is a hydrogen atom or a methanesulphonyl or toluenesulphonyl group, by the elimination of the elements of HT.

Such a reaction will normally take place in the presence of an acid or base catalyst, such as sulphuric or phosphoric acid, acetic anhydride or sodium hyroxide or heat.

Compounds of the formula (XII) wherein T is a hydroxyl group may be prepared by the reaction of a compound of the formula (XI), as hereinbefore defined, with an organometallic compound of the formula MCHR$_8$R$_9$ wherein R$_8$, R$_9$ are as defined with respect to formula (XD) and M is Li, Na, MgI, MgBr or MgCl.

Compounds of the formula (II) wherein X is CHCl may be prepared by the reaction of a compound of the formula (II) wherein X is CHOH with a chlorinating agent.

Suitable chlorinating agents are thionyl chloride and phosphorus pentachloride and in our hands we have found thionyl chloride to be extremely suitable.

The reaction will normally be carried out in an inert organic solvent at a non-extreme temperature.

Suitably the solvent will be benzene or toluene.

Suitably the temperature will be between −10° C. and +100° C.

Compounds of the formula (II) wherein X is CHOH may be prepared by the reaction of the corresponding compound of the formula (II) wherein X is C=O with a reducing agent.

Suitable reducing agents are complex metal hydrides, such as borohydrides or lithium aluminium hydride, or hydrogen in the presence of a transition metal catalyst, such as palladium on charcoal.

The reaction will normally be carried out in an inert solvent at a non-extreme temperature.

Suitably the solvent will be a lower alkanol such as methanol or ethanol when the reducing agent is a borohydride or hydrogen in the presence of a transition metal catalyst, or an ether, for example diethyl ether, when reducing agent is lithium aluminium hydride.

Suitably the temperature will be between −10° C. and +100° C. for example ambient temperature.

Compounds of the formula (II) wherein X is CHR$_{10}$ may be prepared by the reduction of the corresponding compound of the formula (II) wherein X is CR$_{10}$OH.

The reduction will normally be carried out by hydrogenation in the presence of a transition metal catalyst, for example perchloric acid.

Compounds of the formula (II) wherein X is CHR$_{10}$ may also be prepared by the reduction of the corresponding compound of the formula (II) wherein X is

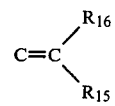

wherein CHR$_{15}$R$_{16}$ is a C$_{1-4}$ alkyl group.

The reduction will normally be carried out by hydrogenation in the presence of a transition metal catalyst such as palladium on charcoal.

These reduction reactions will normally be carried out in an inert organic solvent such as a lower alkanol, for example methanol or ethanol, at a non-extreme temperature such as −10° C. to +100° C., for example ambient temperature.

Compounds of the formula (II) wherein X is C=CR$_{15}$R$_{16}$ may be prepared by the reaction of a compound of the formula (II) wherein X is C=O with a Wittig reagent, for example Ph$_3$P=CR$_{15}$R$_{16}$, or with an organometallic compound wherein M,R$_{15}$ and R$_{16}$ are as hereinbefore defined followed by dehydration.

Compounds of the formula (II) wherein X is CR$_{10}$OH may be prepared by the reaction of a compound of the formula (II) wherein X is C=O with an organometallic compound of the formula MR$_{10}$ wherein M and R$_{10}$ is as hereinbefore defined.

Compounds of the formula (VIII), (X) and (XII) are useful intermediates and as such form part of this invention.

The compounds of the formula (IX) may be prepared by reaction Scheme I.

The following examples are illustrative of the invention.

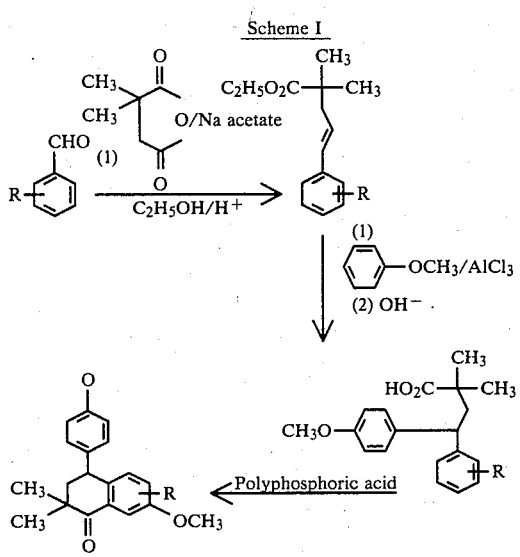

Scheme I

EXAMPLE 1

Ethyl 4-(4-Chlorophenyl)-2,2-dimethylbut-3-enoate

Sodium acetate (22.5 g), 4-chlorobenzaldehyde (47.2 g) and 2,2-dimethylsuccinnic anhydride were heated together under reflux for 48 hr. On cooling, the resulting solid mass was dissolved in sodium carbonate solution and excess aldehyde washed out with light petrol (b.p. 60°–80°). Acidification (dilute HCl) gave the butenoic acid, which was washed with water, dried and esterified with ethanol-concentrated sulphuric acid. Ethyl 4-(4-chlorophenyl)-2,2-dimethylbut-3-enoate was isolated as a pale yellow oil, (54.5 g, 85%).

EXAMPLE 2

4-(4-Chlorophenyl)-4-(4-methoxyphenyl)-2,2-dimethylbutanoic acid

Following the method of Rudenko et al*, anisole was alkylated with ethyl 4-(4-chlorophenyl)-2,2-dimethylbut-3-enoate. Hydrolysis of the ester with potassium hydroxide gave 4-(4-chlorophenyl)-4-(4-methoxyphenyl)-2,2-dimethylbutanoic acid, purified by washing with sodium bicarbonate solution and water. Recrystallization from ethyl acetate-light petrol (b.p. 60°–80°) afforded the acid as white prisms, m.p. 139°–142° (63%).

*M. G. Rudenko, Yu. P. Sobolev, I. B. Gryargnova, T. V. Stukanora, *Neftekhimiya*, 1968, 8, 351; *Chem. Abstr.* 1969, 70, 3473n.

EXAMPLE 3

4-(4-Chlorophenyl)-7-methoxy-2,2-dimethyl-1-tetralone

A mixture of polyphosphoric acid (169 g) and 4-(4-chlorophenyl)-4-(4-methoxyphenyl)-2,2-dimethylbutanoic acid (14.9 g) was stirred at 125°–135° for 80 min. The solution was poured on to crushed ice and the mixture extracted with ethyl acetate. The extracts were washed with sodium bicarbonate solution, dried (MgSO$_4$) and passed down a short alumina column. Removed of the solvent and recrystallization from ether-light petrol (b.p. 60°–80°) furnished 4-(4-chlorophenyl)-7-methoxy-2,2-dimethyl-1-tetralone as white prisms, m.p. 135°–8° (7.2 g, 51%).

EXAMPLE 4

4-(4-Chlorophenyl)-7-hydroxy-2,2-dimethyl-1-tetralone

A solution of 4-(4-chlorophenyl)-7-methoxy-2,2-dimethyl-1-tetralone (16.1 g) in acetic acid (75 ml) and hydrobromic acid (48%, 75 ml) was heated under reflux for 16 hr. The solution was concentrated in vacuo, water was added and the mixture extracted with ethyl acetate. The extracts were washed well with water and sodium bicarbonate solution, dried (MgSO$_4$) and the solvent removed to give 4-(4-chlorophenyl)-7-hydroxy-2,2-dimethyl-1-tetralone as a white solid which was used without purification (14.7 g, 91%).

EXAMPLE 5

4-(4-Chlorophenyl)-2,2-dimethyl-7-(2-dimethylaminoethoxy)-1-tetralone

A mixture of 4-(4-chlorophenyl)-7-hydroxy-2,2-dimethyl-1-tetralone (14.7 g), sodium hydride (80% oil dispersion, 1.65 g) and 2-dimethylaminoethyl chloride (5.8 g) was heated under reflux in toluene (150 ml) for 6 hr. The solvent was removed and the residue shaken with ether-dilute hydrochloric acid. The aqueous layer was separated, basified, extracted with ether and the extract dried (MgSO$_4$). Evaporation gave 4-(4-chlorophenyl)-2,2-dimethyl-7-(2-dimethylaminoethoxy)-1-tetralone as a yellow oil (17 g, 91%) which was contaminated with ether. A portion was converted to the hydrochloride salt (64%), which crystallised as white prisms from ethanol-ether, m.p. 209°–211°.

EXAMPLE 6

4-(4-Chlorophenyl)-1-hydroxy-2,2-dimethyl-7-(2-dimethylaminoethoxy)tetralin

A solution of 4-(4-chlorophenyl)-2,2-dimethyl-7-(2-dimethylaminoethoxy)-1-tetralone (13.6 g) in dry ether (75 ml) was added to a stirred suspension of aluminium lithium hydride (1.3 g) in dry ether (75 ml) over 40 min. The mixture was heated under reflux a further 45 min., cooled, a few drops of dilute sodium hydroxide solution added, and the ether solution decanted off. The remaining pasty mass was extracted with hot ether, and the combined ether solutions were dried (MgSO$_4$). Removal of the solvent gave 4-(4-chlorophenyl)-1-hydroxy-2,2-dimethyl-7-(2-dimethylaminoethoxy)tetralin as a white foam. (13.3 g, 98%). The hydrochloride salt formed white prisms from ethanol-ether, m.p. 235°–7°.

EXAMPLE 7

1-Chloro-4-(4-chlorophenyl)-2,2-dimethyl-7-(2-dimethylaminoethoxy)tetralin

Thionyl chloride (3 ml) was added dropwise to a stirred solution of 4-(4-chlorophenyl)-1-hydroxy-2,2-dimethyl-7-(2-dimethylaminoethoxy)tetralin (2.0 g) in benzene (50 ml), the temperature being maintained at 5°–10°. After being stirred at room temperature for 16 hr., the solution was taken to dryness in vacuo, the residue shaken with ether-sodium carbonate solution and the ether extract dried (MgSO$_4$). Addition of ethereal hydrogen chloride solution precipitated a viscous oil, which was separated by decantation and redissolved in ethanol. Addition of ether and cooling gave 1-chloro-4-(4-chlorophenyl)-2,2-dimethyl-7-(2-dimethylaminoethoxy)tetralin as the hydrochloride salt, m.p. 185°–210° approx. (0.93 g, 41%).

EXAMPLE 8

4-(4-Chlorophenyl)-2,2-dimethyl-7-(2-dimethylaminoethoxy)-1-methylidene tetralin An ethereal solution of methyllithium (50 ml, 1.9 M) was added over 45 min. to a stirred solution of 4-(4-chlorophenyl)-2,2-dimethyl-7-(2-dimethylaminoethoxy)-1-tetralone (18.5 g) in dry ether (150 ml) and the mixture heated under reflux for 30 min. After cooling, excess methyllithium was decomposed with water, the ether layer was separated, dried (MgSO4) and treated with a solution of hydrogen chloride in ether. The hydrochloride salt of 4-(4-chlorophenyl)-2,2-dimethyl-7-(2-dimethylaminoethoxy)-1-methylidene tetralin precipitated as a white solid (15.6 g, 77%). A portion was recrystallized from ethanol-ether, m.p. 233°–235°.

EXAMPLE 9

4-(4-Chlorophenyl)-1,2,2-trimethyl-7-(2-dimethylaminoethoxy)tetralin

A solution of 4-(4-chlorophenyl)-2,2-dimethyl-7-(2-dimethylaminoethoxy)-1-methylidene tetralin hydrochloride (4 g) in ethanol (150 ml) was hydrogenated in the presence of 10% palladium on charcoal (0.4 g) until hydrogen uptake was complete. After filtration the solvent was removed in vacuo to give 4-(4-chlorophenyl)-1,2,2-trimethyl-7-(2-dimethylaminoethoxy)tetralin hydrochloride. Recrystallisation from ethanol-ether gave white prisms, m.p. 173°–6° (3.6 g, 90%).

EXAMPLE 10

3-Trifluoromethyl-4'-methoxybenzophenone

Aluminium chloride (15.5 g) was added over 2 hours in small portions to an ice-cooled solution of 3-trifluoromethylbenzoyl chloride (21.7 g) and anisole (12.5 g) in dichloromethane. After a further 2 hours at room temperature, the mixture was poured on to ice, extracted with dichloromethane and the extracts washed with water and dried (MgSO4). Removal of solvent gave a solid which was recrystallised first from light petrol (b.p. 60°–80°) and then from ethanol-water, giving white prisms of the ketone, m.p. 62.5°–63.5°, (17.5 g, 60%).

EXAMPLE 11

Ethyl 3-(3-trifluoromethylphenyl)-3-(4-methoxyphenyl)propionate

A mixture of 3-trifluoromethyl-4'-methoxy benzophenone (15.0 g) and sodium hydride (80% oil dispersion, 2.0 g) in dry dimethoxyethane (150 ml), under nitrogen, was cooled to 0° and triethyl phosphonoacetate (12.75 ml) was added. The mixture was gently refluxed for 70 hrs., cooled, poured into water, extracted with ether, the ether extracts washed with water, dried (MgSO4) and the solvent removed at the pump. Without purification, the light brown oil was dissolved in ethanol (200 ml) and hydrogenated over palladium (10% on charcoal, 2 g). After filtration and removal of solvent, the product was dissolved in ether, eluted through a short alumina column and solvent removed to give ethyl 3-(3-trifluoromethylphenyl)-3-(4-methoxyphenyl)propionate as a colourless oil (16.9 g, 90%).

EXAMPLE 12

4-(3-trifluoromethylphenyl)-7-methoxy-1-tetralone

Ethyl 3-(3-trifluoromethylphenyl)-3-(4-methoxyphenyl)propionate was converted to 4-(3-trifluoromethylphenyl)-4-(4-methoxyphenyl) butanoic acid by standard methods, viz. reduction of the propionate ester to the propanol (93%) tosylation (81%), conversion to the butyronitrile (67%) and hydrolysis to the butanoic acid (85%), which was obtained as a pale yellow oil. This oil (10 g) was stirred overnight at room temperature in a solution of methanesulphonic acid (100 g) and phosphorus pentoxide (21 g). The mixture was poured onto ice, extracted with ether, the extracts washed with dilute sodium hydroxide, dried (MgSO4) and filtered through a short column of alumina. Removal of the ether gave 4-(3-trifluoromethylphenyl)-7-methoxy-1-tetralone as a pale yellow oil (7.65 g, 81%).

EXAMPLE 13

4-(3-trifluoromethylphenyl)-7-(2-dimethylaminoethoxy)-1-tetralone

A solution of 4-(3-trifluoromethylphenyl)-7-methoxy-1-tetralone (3.1 g) in acetic acid (25 ml) and hydrobromic acid (48%, 25 ml) was heated under reflux for 16 hr. The solution was concentrated in vacuo, water was added and the mixture extracted with ethyl acetate, the extracts washed well with water and sodium bicarbonate solution, dried (MgSO4) and the solvent removed to leave 4-(3-trifluoromethylphenyl)-7-hydroxy-1-tetralone as a dark green oil, used without purification. The oil was taken up in dry toluene (50 ml), sodium hydride (80%) dispersion in oil, 0.45 g) added and the mixture heated to the point of reflux. Dimethylaminoethyl chloride (1.2 g) was added to the cooled mixture, which was then heated under reflux for 5 hr. The solvent was removed, ethyl acetate-water added and the organic layer separated, washed with sodium bicarbonate solution, dried (K2CO3), passed through a short alumina column, and the solvent removed to give impure 4-(3-trifluoromethylphenyl)-7-(2-dimethylaminoethoxy)-1-tetralone. The pure hydrochloride was obtained as off-white prisms after two recrystallisations from ether-ethanol (0.9 g, 22%), m.p. 203°–207°.

EXAMPLE 14

4-(3-Trifluoromethylphenyl)-2,2-dimethyl-7-(2-dimethylaminoethoxy)-1-tetralone 4-(3-Trifluoromethylphenyl)-7-methoxy-1-tetralone was converted to 4-(3-trifluoromethylphenyl)-7-methoxy-2,2-dimethyl-1-tetralone using methyl iodide-potassium t-butoxide in t-butanol (88%). Dimethylation and alkylation with dimethylaminoethylchloride, as described above, gave 4-(3-trifluoromethylphenyl)-2,2-dimethyl-7-(2-dimethylaminoethoxy)-1-tetralone, obtained, after purification by chromatography on alumina with ether-light petrol (b.p. 60°–80°), as a brown oil (40%). A portion was converted to the hydrochloride salt (92%) which formed white prisms from ethanol-ether, m.p. 208°–209°.

EXAMPLE 15

4-(4-Fluorophenyl)-2,2-dimethyl-7-(2-dimethylaminoethoxy)-1-tetralone 4-(4-Fluorophenyl)-7-hydroxy-2,2-dimethyl-1-tetralone, m.p. 136.5°–138°, was prepared from 4-fluorobenzyaldehyde by an analogous process to that described for the 4-(4-chloro) analogue.

A mixture of the above phenol (3.00 g) and sodium hydride (0.50 g., 80% dispersion in oil) was stirred and brought to reflux. To the resulting pale yellow suspension was added dropwise over 15 mins. a solution of 2-dimethylaminoethyl chloride (1.25 g) in toluene (10 ml) and the resulting mixture was heated to reflux also stirring for a further 2.75 hours. Isolation in the normal manner by acid extraction gave 4-(4-fluorophenyl)-2,2-dimethyl-7-(2-dimethylaminoethoxy)-1-tetralone (3.34 g, 89%). The hydrochloride salt has m.p. 189°–192.5°.

EXAMPLE 16

4-(4-chlorophenyl)-7-(2,3-epoxypropoxy)-2,2-dimethyl-1-tetralone

A mixture of 4(4-chlorophenyl)-7-hydroxy-2,2-dimethyl-1-tetralone (17.6 g), epichlorohydrin (30 ml) and potassium carbonate (6.0 g) was heated under reflux in acetone (30 ml) for 24 hr. The hot mixture was filtered and evaporation of the filtrate in vacuo gave 4-(4-chlorphenyl)-7-(2,3-epoxypropoxy)-2,2-dimethyl-1-tetralone as a light yellow gum (8.4 g, 93%).

EXAMPLE 17

4-(4-chlorophenyl)-7-(2-hydroxy-3-dimethylaminopropoxy)-2,2-dimethyl-1-tetralone To a solution of 4-(4-chlorophenyl)-7-(2,3-epoxypropoxy)-2,2-dimethyl-1-tetralone (4.0 g) in ethanol (40 ml) was added to 40% ethanol dimethylamine solution (20 ml), and the mixture left to stand overnight. The solvent was removed and the residue shaken with ether-dilute hydrochloric acid. The aqueous layer was separated, basified, extracted with ether, and the extract dried (MgSO$_4$). Evaporation gave 4-(4-chlorophenyl)-7-(2-hydroxy-3-dimethylaminopropoxy)-1-tetralone (3.2 g, 71%) as a gummy solid.

NMR$\delta$CDCl$_3$ (7.3, multiplet, 7H; 4.0, multiplet, 4H; 3.4, multiplet, 3H; 2.9, singlet, 6H; 2.0, doublet, 2H; 1.2, singlet, 6H).

D$_2$O shake (7.3, multiplet, 7H; 4.0, multiplet, 4H; 3.4, doublet, 2H; 2.9, singlet, 6H; 2.0 doublet, 2H; 1.2, singlet, 6H).

EXAMPLE 18

4-(4-chlorophenyl)-7-(2-hydroxy-3-methylaminopropoxy)-2,2-dimethyl-1-tetralone

To a solution of 4-(4-chlorophenyl)-7-(2,3-epoxypropoxy)-2,2-dimethyl-1-tetralone (3.7 g) in ethanol (25 ml) was added methylamine (8 ml) in ethanol (8 ml). The mixture was allowed to stand overnight. The solvent was removed and the residue shaken with ether-dilute hydrochloric acid. The aqueous layer was separated basified, extracted with ether and the extract dried (MgSO$_4$). Evaporation gave 4(4-chlorophenyl)-7-(2-hydroxy-3-methylaminopropoxy)-2,2-dimethyl-1-tetralone as a semi-solid foam.

NMR $\delta$ CDCl$_3$ (7.3, multiplet, 7H; 4.0, multiplet, 4H; 3.4, broad singlet, 2H; 2.7, doublet, 2H; 2.4, singlet, 3H; 2.0, doublet, 2H; 1.2, singlet, 6H).

D$_2$O shake (7.3, multiplet, 7H; 4.0, multiplet, 4H; 2.7, doublet, 2H; 2.4, singlet, 3H; 2.0, doublet, 2H; 1.2, singlet, 6H). N-H and O-H broad singlet 3.48.

EXAMPLE 19

4-(4-chlorophenyl)-7-(2-benzylmethylaminoethoxy)-2,2-dimethyl-1-tetralone

A mixture of 4-(4-chlorophenyl)-7-hydroxy-2,2-dimethyl-1-tetralone (3.7 g) and sodium hydride (0.8 g, 60% dispersion in oil) was refluxed in toluene (25 ml) until evolution of hydrogen had ceased. A solution of N-2-chloro-N-methylbenzylamine (3.6 g) in toluene (15 ml) was added dropwise, and the mixture refluxed for 3 hr. The solvent was removed and the residue shaken with ether-dilute hydrochloric acid. The aqueous layer was separated, basified, extracted with ether and the extract dried (MgSO$_4$). Evaporation gave only unreacted N-2-chloroethyl-N-methylbenzylamine. Evaporation of the ether layer from acid extraction gave a colourless solid. Recrystallisation of this solid from petrol/ethyl acetate gave 4-(4-chlorophenyl)-7-(2-benzylmethylaminoethoxy)-2, 2-dimethyl-1-tetralone hydrochloride (4.3 g, 72%) m.pt. 179°–80° C. as colourless flakes.

EXAMPLE 20

4-(4-chlorophenyl)-2,2-dimethyl-7-(2-methylaminoethoxy)-1-tetralone

A solution of 4-(4-chlorophenyl)-7-(2-benzylmethylaminoethoxy)-2,2-dimethyl-1-tetralone hydrochloride (4.3 g) in ethanol (100 ml) was hydrogenated in the presence of 10% palladium on charcoal (0.43 g) until hydrogen uptake was complete. After filtration the solvent was removed in vacuo to give 4-(4-chlorophenyl)-2,2-dimethyl-7-(2-methylaminoethoxy)-1-tetralone hydrochloride. Recrystallisation from ether-ethyl acetate gave white crystals m.p. 150°–3° (2.6 g, 74%).

NMR $\delta$ CDCl$_3$ (2.9, broad multiplet, 7H; 5.7, broad multiplet, 3H; 6.6, triplet, 2H; 7.2, singlet, 3H; 7.9, broad dublet, 2H; 8.8, singlet, 6H).

EXAMPLE 21

4-(3,4-Dichlorophenyl)-7-hydroxy-2,2-dimethyl-1-tetralone

The above compound was made by the same route as 4-(4-chlorophenyl)-7-hydroxy-2,2-dimethyl-1-tetralone. Overall yield from 3,4-dichlorobenzaldehyde was 19%.

EXAMPLE 22

4-(3,4-Dichlorophenyl)-2,2-dimethyl-7-(2-dimethylaminoethoxy)-1-tetralone

A mixture of 4-(3,4-dichlorophenyl)-7-hydroxy-2,2-dimethyl-1-tetralone (2.3 g) and sodium hydride (0.4 g, 60% dispersion in oil) was refluxed in toluene (20 ml) until evolution of hydrogen had ceased. A solution of 2-dimethylaminoethylchloride (1.2 g) in toluene (15 ml) was added dropwise and the mixture refluxed for 3 hr. The solvent was removed and the residue shaken with ether-dilute hydrochloric acid. The aqueous layer was separated, basified, extracted with ether and the extract dried (MgSO$_4$). Evaporation gave the product as the free base, which was converted to the hydrochloride salt. Recrystallisation from ether-ethyl acetate gave 4-(3,4-dichlorophenyl)-2,2-dimethyl-7-(2-dimethylaminoethoxy)-1-tetralone hydrochloride as white crystals, (2.2 g, 72%) m.p. 180°–5° C.

EXAMPLE 23

4-(3,4-Dichlorophenyl)-7-(2,3-epoxypropoxy)-2,2-dimethyl-1-tetralone

A mixture of 4-(3,4-dichlorophenyl)-7-hydroxy-2,2-dimethyl-1-tetralone (2.9 g), epichlorohydrin (10 ml) and potassium carbonate (2 g) was heated under reflux in acetone (10 ml) for 24 hr. The hot mixture was filtered and evaporation of the filtrate in vacuo gave 4-(3,4-dichlorophenyl)-7-(2,3-epoxypropoxy)-2,2-dimethyl-1-tetralone as a yellow gum (3.2 g, 94%).

EXAMPLE 24

4-(3,4-Dichlorophenyl)-7-(2-hydroxy-3-methylaminopropoxy)-2,2-dimethyl-1-tetralone To a solution of 4-(3,4-dichlorophenyl)-7-(2,3-epoxypropoxy)-2,2-dimethyl-1-tetralone (3.2 g) in ethanol (30 ml) was added a solution of methylamine (10 ml) in ethanol (10 ml) and the mixture left to stand overnight. The solvent was removed and the residue shaken with ether-dilute hydrochloric acid. The aqueous layer was separated, basified, extracted with ether and the extract dried (MgSO₄). Evaporation gave the product as the free base, which was converted to the hydrochloride salt. Recrystallisation from petrol/ether gave 4-(3,4-dichlorophenyl)-7-(2-hydroxy-3-methylaminopropoxy)-1-tetralone hydrochloride as white crystals (2.5 g, 72%) m.p. 105°–10°(dec).

EXAMPLE 25

The useful mood-modifying activity of the compounds of this invention may be determined by standard tests such as the Reserpine Prevention test which demonstrates the ability of the compounds to prevent reserpine-induced hypothermia in mice. The results given in Table 1 were obtained for compounds of the formula (XIII):

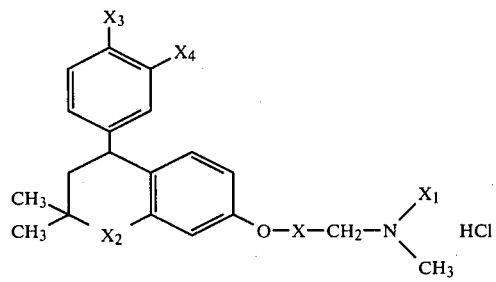

(XIII)

The useful anorexic activity of 4-(4-chlorophenyl)-2,2-dimethyl-7-(2-dimethylaminoethoxy)-1-methylidene tetralin and 4-(4-chlorophenyl-1,2,2,-trimethyl-7-(2-dimethylaminoethoxy) tetralin were determined by the oral administration to hungry rats of the compound and measuring the reduction in their food intake. The results are as follows:

4-(4-chlorophenyl)-2,2-dimethyl-7-(2-dimethylaminoethoxy)-1-methylidene tetralin gave a 51% reduction in food intake when administered orally at 10 mg./kg.

4-(4-chlorophenyl-1,2,2,-trimethyl-7-(2-dimethylaminoethoxy) tetralin gave 35% reduction in food intake when administered orally at 10 mg./kg.

We claim:

1. A compound of the formula (II):

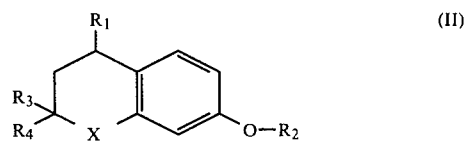

(II)

or a pharmaceutically acceptable salt thereof, wherein R₁ is phenyl or naphthyl or phenyl or naphthyl each substituted by one or two halogen atoms, alkyl of 1 to 4 carbon atoms, alkoxy of 1 to 4 carbon atoms, trifluoromethyl, nitro, hydroxy, or trifluoromethylthio, R₂ is

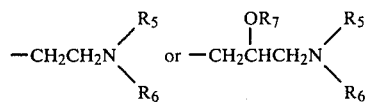

wherein R₅ is hydrogen or alkyl of 1 to 6 carbon atoms, R₆ is hydrogen, or alkyl of 1 to 6 carbon atoms, and R₇ is hydrogen; R₃ and R₄ are each hydrogen or alkyl of 1 to 4 carbon atoms, and X is CO, CHOH, CHCl or

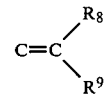

wherein R₈ and R₉ are each hydrogen, alkyl of 1 to 4 carbon atoms, CR₁₀OH or CHR₁₀ wherein R₁₀ is alkyl of 1 to 4 carbon atoms.

2. A compound according to claim 1 wherein R₁ is phenyl substituted by fluorine, chlorine or trifluoromethyl, or is naphthyl.

3. A compound according to claim 1 wherein R₅ is hydrogen or methyl.

4. A compound according to claim 1 wherein R₆ is hydrogen or methyl or ethyl.

TABLE 1

| | | | | | Dose at which Certain Compounds of the Invention are Active on the Reserpine Prevention Test in Mice | | |
|---|---|---|---|---|---|---|---|
| X | X₁ | X₂ | X₃ | X₄ | Approximate Dose required mg/kg | Min Dose (mg/kg) at which deaths occurred | Approximate oral LD₅₀ in mice in mg/kg |
| —CH₂— | CH₃ | C=O | Cl | H | 0.03 | 10 | 55 |
| —CH₂— | CH₃ | CHOH | Cl | H | 0.1 | 3 | 11 |
| —CH₂— | CH₃ | CHCl | Cl | H | 0.1 | 30 | 33 |
| —CH₂— | CH₃ | CHCH₃ | Cl | H | 3 | >100 | >100 |
| —CH₂— | CH₃ | C=O | Cl | Cl | 1 | 10 | 10–30 |
| —CH₂— | CH₃ | C=O | H | CF₃ | 3 | >100 | >100 |
| —CH₂—CH(OH)— | H | C=O | Cl | Cl | 1 | >100 | 100 |

5. A compound according to claim 1 wherein $R_3$ and $R_4$ are each hydrogen or methyl.

6. A compound according to claim 1 wherein X is

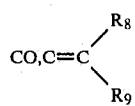

or $CHR_{10}$ wherein $R_8$ and $R_9$ are each hydrogen or alkyl of 1 to 4 carbon atoms and $R_{10}$ is alkyl of 1 to 4 carbon atoms.

7. A compound of the formula (III):

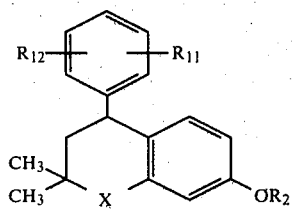

(III)

or a pharmaceutically acceptable salt thereof wherein X is CO,

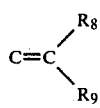

or $CHR_{10}$ wherein $R_8$ and $R_9$ are each hydrogen or alkyl of 1 to 4 carbon atoms and $R_{10}$ is alkyl of 1 to 4 carbon atoms, $R_2$ is a group of the sub-formulae (f)-(i):

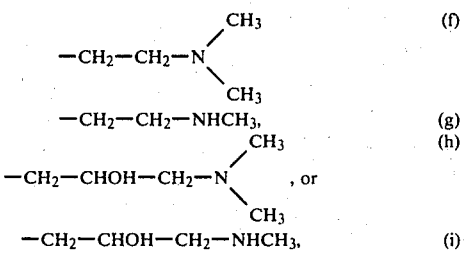

$R_{11}$ is chlorine, bromine, fluorine, trifluoromethyl, or nitro and $R_{12}$ is hydrogen or $R_{11}$ and $R_{12}$ are both chlorine or fluorine.

8. A compound according to claim 7 wherein $R_{11}$ is chlorine, fluorine or trifluoromethyl and $R_{12}$ is hydrogen.

9. A compound of the formula (VI):

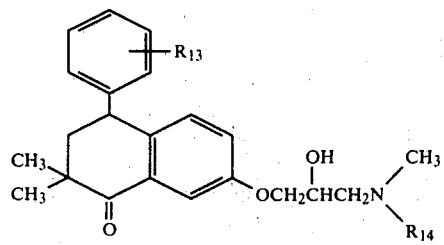

(VI)

or a pharmaceutically acceptable salt thereof wherein $R_{13}$ is fluorine, chlorine, nitro or trifluoromethyl and $R_{14}$ is hydrogen, methyl, ethyl or benzyl.

10. A compound according to claim 9 wherein $R_{13}$ is fluorine or chlorine.

11. A compound according to claim 10 wherein $R_{14}$ is methyl.

12. A compound according to claim 1 wherein $R_8$ and $R_9$ are each hydrogen.

13. A compound according to claim 1 wherein $R_2$ is a group of the sub-formulae:

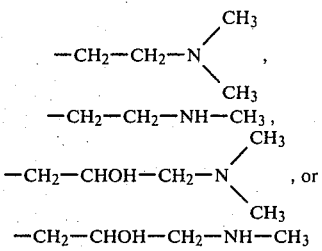

14. A compound according to claim 7 wherein $R_{11}$ is chlorine or fluorine.

15. A compound according to claim 1 in the form of an acid addition salt selected from citrate, acetate, propionate, lactate, tartrate, mandelate, succinate, oleate, glutarate, gluconate, methylene sulfonate, toluene sulfonate, sulfate, phosphate, hydrobromide and hydrochloride.

16. A compound according to claim 1 wherein $R_5$ is hydrogen or alkyl of 1 to 6 carbon atoms, $R_6$ is hydrogen, alkyl of 1 to 6 carbon atoms, phenyl, tolyl or benzyl and $R_7$ is hydrogen.

17. The compound according to claim 1 which is 4-(3-trifluoromethylphenyl)-2,2-dimethyl-7-(2-dimethylaminoethoxy)-1-tetralone or a pharmaceutically acceptable acid addition salt thereof.

18. The compound according to claim 1 which is 4-(4-fluorophenyl)-2,2-dimethyl-7-(2-dimethylaminoethoxy)-1-tetralone or a pharmaceutically acceptable acid addition salt thereof.

19. The compound according to claim 1 which is 4-(4-chlorophenyl)-7-(2-hydroxy-3-dimethylaminopropoxy)-2,2-dimethyl-1-tetralone or a pharmaceutically acceptable acid addition salt thereof.

20. The compound according to claim 1 which is 4-(4-chlorophenyl)-7-(2-benzylmethylaminoethoxy)-2,2-dimethyl-1-tetralone or a pharmaceutically acceptable acid addition salt thereof.

21. The compound according to claim 1 which is 4-(4-chlorophenyl)-2,2-dimethyl-7-(2-methylaminoethoxy)-1-tetralone or a pharmaceutically acceptable acid addition salt thereof.

22. The compound according to claim 1 which is 4-(3,4-dichlorophenyl)-2,2-dimethyl-7-(2-dimethylaminoethoxy)-1-tetralone or a pharmaceutically acceptable acid addition salt thereof.

23. The compound according to claim 1 which is 4-(3,4-dichlorophenyl)-7-(2-hydroxy-3-methylaminopropoxy)-2,2-dimethyl-1-tetralone or a pharmaceutically acceptable acid addition salt thereof.

24. The compound according to claim 1 which is 4-(4-chlorophenyl)-7-(2-hydroxy-3-methylaminopropoxy)-2,2-dimethyl-1-tetralone or a pharmaceutically acceptable acid addition salt thereof.

* * * * *